United States Patent [19]

Collen

[11] Patent Number: 5,695,754
[45] Date of Patent: Dec. 9, 1997

[54] STAPHYLOKINASE DERIVATIVES

[75] Inventor: Desire Collen, Schoonzichtlaan 20, B-3020 Winksele-Herent, Belgium

[73] Assignees: Leuven Research & Development VZW; Desire Collen, both of Belgium

[21] Appl. No.: 371,505

[22] Filed: Jan. 11, 1995

[30] Foreign Application Priority Data

Jan. 6, 1995 [EP] European Pat. Off. ............... 95200023

[51] Int. Cl.$^6$ .............................. A61K 38/48; C12N 9/52
[52] U.S. Cl. ........................................ 424/94.64; 435/220
[58] Field of Search .......................... 424/94.61, 94.64; 435/200, 212, 219, 220

[56] References Cited

PUBLICATIONS

Schlott, et al. *Biochimica et Biophysica Acta* 1204:235–242 (1994).

*Primary Examiner*—Vasu S. Jagannathan
*Assistant Examiner*—Brian K. Lathrop
*Attorney, Agent, or Firm*—Webb Ziesenheim Bruening Logsdon Orkin & Hanson, P.C.

[57] ABSTRACT

A method for producing the derivatives of the invention by preparing a DNA fragment comprising at least the part of the coding sequence of staphylokinase that provides for its biological activity; performing in vitro site-directed mutagenesis on the DNA fragment to replace one or more codons for wild-type amino acids by a codon for another amino acid; cloning the mutated DNA fragment in a suitable vector; transforming or transfecting a suitable host cell with the vector; and culturing the host cell under conditions suitable for expressing the DNA fragment. Preferably the DNA fragment is a 466 bp EcoRI-HINDIII fragment of the plasmid pMEX602SAK, the in vitro site-directed mutagenesis is performed by an oligonucleotide-directed mutagenesis system using the plasmid pMa/c and the repair deficient *E. coli* strain WK6MutS, and the mutated DNA fragment is cloned in *E. coli* strain-WK6. The invention also relates to pharmaceutical compositions comprising at least one of the staphylokinase derivatives according to the invention together with a suitable excipient, for treatment of arterial thrombosis.

13 Claims, 2 Drawing Sheets

```
 1                                                                        14
 Ser Ser Ser Phe Asp Lys Gly Lys Tyr Lys Lys Gly Asp Asp
                 └──┬──┘     └──┬──┘     └────┬────┘
                    20          21            1

15                                                                       28
Ala Ser Tyr Phe Glu Pro Thr Gly Pro Tyr Leu Met Val Asn
                └─┬─┘
                  22

29                                                                       42
Val Thr Gly Val Asp Ser Lys Gly Asn Glu Leu Leu Ser Pro
                └──┬──┘ └──┬──┘
                   2       3

43                                                                       56
His Tyr Val Glu Phe Pro Ile Lys Pro Gly Thr Thr Leu Thr
            └─────────┬─────────┘
                      4

57                                                                       70
Lys Glu Lys Ile Glu Tyr Tyr Val Glu Trp Ala Leu Asp Ala
└──┬──┘     └──────┬──────┘ └──────┬──────┘
   5               6                7

71                                                                       84
Thr Ala Tyr Lys Glu Phe Arg Val Val Glu Leu Asp Pro Ser
            └────┬────┘             └────┬────┘
                 8                       9

85                                                                       98
Ala Lys Ile Glu Val Thr Tyr Tyr Asp Lys Asn Lys Lys Lys
    └──┬──┘                  └──┬──┘     └──┬──┘
       10                       11          12

99                                                                      112
Glu Glu Thr Lys Ser Phe Pro Ile Thr Glu Lys Gly Phe Val
└┬┘                              └──┬──┘
 13                                 15
└───┬───┘
   14

113                                                                     126
Val Pro Asp Leu Ser Glu His Ile Lys Asn Pro Gly Phe Asn
        └────────┬────────┘ └──┬──┘
                 16            17

127                        136
Leu Ile Thr Lys Val Val Ile Glu Lys Lys
            └┬┘              └──┬──┘
             18                 19
```

FIG.1

STAPHYLOKINASE DERIVATIVES

This invention relates to new staphylokinase derivatives with reduced immunogenicity, their production and use in the treatment of arterial thrombosis and for the preparation of a pharmaceutical composition for treating arterial thrombosis. More in particular it relates to the use of engineered staphylokinase derivatives for the preparation of a pharmaceutical composition for treating myocardial infarction.

Thrombotic complications of cardiovascular diseases are a main cause of death and disability and, consequently, thrombolysis (i.e. pharmacological dissolution of the blood clot) could favorably influence the outcome of such life-threatening diseases as myocardial infarction, cerebrovascular thrombosis and venous thromboembolism. Thrombolytic agents are plasminogen activators that convert plasminogen, the inactive proenzyme of the fibrinolytic system in blood, to the proteolytic enzyme plasmin. Plasmin dissolves the fibrin of a blood clot, but may also degrade normal components of the hemostatic system and induce the so-called "lytic state". Physiological fibrinolysis however is fibrin-oriented as a result of specific molecular, interactions between tissue-type plasminogen activator, fibrin, plasmin (ogen) and $\alpha_2$-antiplasmin (1,2).

Currently, six thrombolytic agents are either approved for clinical use or under clinical investigation in patients with acute myocardial infarction. These include streptokinase, urokinase, recombinant tissue-type plasminogen activator (rt-PA) or derivatives of it, anisoylated plasminogen streptokinase activator complex (APSAC), recombinant single chain urokinase-type plasminogen activator (rscu-PA, recombinant prourokinase), and recombinant staphylokinase (Sak) (2,3). In patients with acute myocardial infarction, reduction of infarct size, preservation of ventricular function and reduction in mortality has been observed following treatment with either streptokinase, rt-PA or APSAC (2).

One of the thrombolytic agents currently routinely used in therapy is streptokinase, a $M_r$ 45,000 protein secreted by β-hemolytic streptococci. Its administration is however associated with extensive systemic fibrinogen breakdown and its efficacy for coronary thrombolysis in patients with evolving acute myocardial infarction is limited, amounting to approximately 50 percent coronary artery recanalization within 90 minutes (2). Furthermore, exposure to streptokinase provokes allergic reaction in about 5 percent of treated patients and consistently induces specific antibody formation which precludes its repeated use within months or years (4).

Staphylokinase, a protein produced by certain strains of *Staphylococcus aureus*, which was shown to have profibrinolytic properties more than 4 decades ago (5–7), also appears to constitute a potent thrombolytic agent in patients with acute myocardial infarction (8). The staphylokinase gene has been cloned from the bacteriophages sakOC (9) and sak42D (10) as well as from the genomic DNA (sakSTAR) of a lysogenic *Staphylococcus aureus* strain (11). It has been expressed under the control of the λPR promoter and its own translation signals in *Escherichia coli* and also under the control of its neutral promoter and translation signals in *Bacillus subtilis* or *Escherichia coli*, resulting in accumulation of the gene product in the periplasmic space or in the culture medium, respectively (10–13).

The staphylokinase gene encodes a protein of 163 amino acids, with amino acid 28 corresponding to the $NH_2$-terminal residue of full length mature staphylokinase (10, 14,15). The protein sequence of the wild-type variant Sak-STAR (15) is represented in FIG. 1 (SEQ ID NO:2). Only four nucleotide differences were found in the coding regions of the sakOC, sak42D and sakSTAR genes, one of which constituted a silent mutation (10,14,15).

Several molecular forms of staphylokinase have been purified with slightly different $M_r$ (16,500 to 18,000 on SDS-PAGE) and iso-electric points (11–13). Lower $M_r$ derivatives of mature staphylokinase were obtained lacking the 6 (Sak-Δ6) or the 10 (Sak-Δ10) $NH_2$-terminal amino acids. Upon interaction with plasmin(ogen) in a buffer milieu, mature staphylokinase ($NH_2$-terminal Ser-Ser-Ser) is rapidly and quantitatively converted to Sak-Δ10 ($NH_2$-terminal Lys-Gly-Asp-). Mature staphylokinase and Sak-Δ10 were shown to have the same fibrinolytic activity (11,12).

The amino acid in position 26 appears to be of crucial importance for the activation of plasminogen by staphylokinase. Indeed, substitution of the unique Met residue in position 26 with either Arg or Val results in loss of the functional activity, whereas substitution with Leu or Cys has little or no effect on the activity (16). Because none of the single amino acid exchanges causes significant changes of the solution structure of the mutant proteins the mechanism of this differential behavior remains enigmatic.

In a plasma milieu, staphylokinase is able to dissolve fibrin clots without associated fibrinogen degradation (17–19). This fibrin-specificity of staphylokinase is the result of reduced inhibition by $\alpha_2$-antiplasmin of plasmin-.staphylokinase complex following inhibition by $\alpha_2$-antiplasmin, and prevention of the conversion of circulating plasminogen.staphylokinase to plasmin.staphylokinase by $\alpha_2$-antiplasmin (20–22). In several experimental animal models, staphylokinase appears to be equipotent to streptokinase for the dissolution of whole blood or plasma clots, but significantly more potent for the dissolutions of platelet-rich or retracted thrombi (23,24).

The encouraging results obtained with staphylokinase in animal models of thrombosis, have formed the basis for its evaluation, on a pilot scale, in patients with acute myocardial infarction (3,25). In 4 of 5 patients with acute myocardial infarction 10 mg recombinant staphylokinase (SakSTAR), given intravenously over 30 min, was found to induce angiographically documented coronary artery recanalization with 40 minutes. Plasma fibrinogen and $\alpha_2$-antiplasmin levels were unaffected (residual levels at 40 min. of 90–95% of baseline) and allergic reactions were not observed (3). In a second series of 5 patients with acute coronary occlusion, intravenous administration of 10 mg staphylokinase (SakSTAR) over 30 min induced recanalization in all patients within 20 min, without associated fibrinogen degradation (25). Control angiography at 24 hours showed that recanalization persisted.

The immunogenicity of staphylokinase (SakSTAR) as compared to streptokinase was studied in dogs (23) and baboons (24). In aggregate, these experimental animal data suggested a lower immunogenicity of staphylokinase as compared to streptokinase. However, in the first 5 patients with acute myocardial infarction given a intravenous infusion of 10 mg staphylokinase over 30 min, neutralizing antibody titers against staphylokinase (SakSTAR) were low at baseline and up to 6 days after infusion, but high titers (staphylokinase neutralizing titers of 12–42 μg/ml plasma) of antibodies were consistently demonstrable in plasma at 14–35 days (3). These observations were fully confirmed in the second pilot trail in 5 patients (25). Thus with respect to immunogenicity, the initial observations in man were not as encouraging as the experience in experimental animals.

Thus, like streptokinase, staphylokinase administration would be restricted to single use. However, the absence of cross-reactivity of induced antibodies against staphylokinase and streptokinase (26,27) suggests that the administration of both substances would not be mutually exclusive.

The intrinsic immunogenicity of streptokinase and staphylokinase clearly hampers their unrestricted use. Not only will patients with preexisting high antibody titers be refractory to the thrombolytic effect of these agents, but allergic side effects and occasional life-threatening anaphylaxis may occur (28). Because both streptokinase and staphylokinase are heterologous proteins, it is not obvious that their immunogenicity could be reduced by protein engineering. Indeed, no successful attempts to generate active low molecular weight fragments from streptokinase have been reported. In staphylokinase, deletion of the NH$_2$-terminal 15 amino acids or the COOH-terminal 2 amino acids inactivates the molecule, which in addition is very sensitive to inactivation by site-specific mutagenesis (25,29).

Nevertheless, we have, surprisingly, found that the wild-type staphylokinase variant SakSTAR (8,15) contains three non-overlapping immunodominant epitopes, at least two of which can be eliminated by specific site-directed mutagenesis, without inactivation of the molecule. These engineered staphylokinase variants are less reactive with antibodies elicited in patients treated with wild-type staphylokinase, and are significantly less immunogenic than wild-type staphylokinase, as demonstrated in a rabbit model.

BRIEF DESCRIPTION OF THE DRAWINGS

FIG. 1 contains the amino acid sequence of staphylokinase and the amino acid clusters of the present invention.

DETAILED DESCRIPTION OF THE INVENTION

Figure 2:
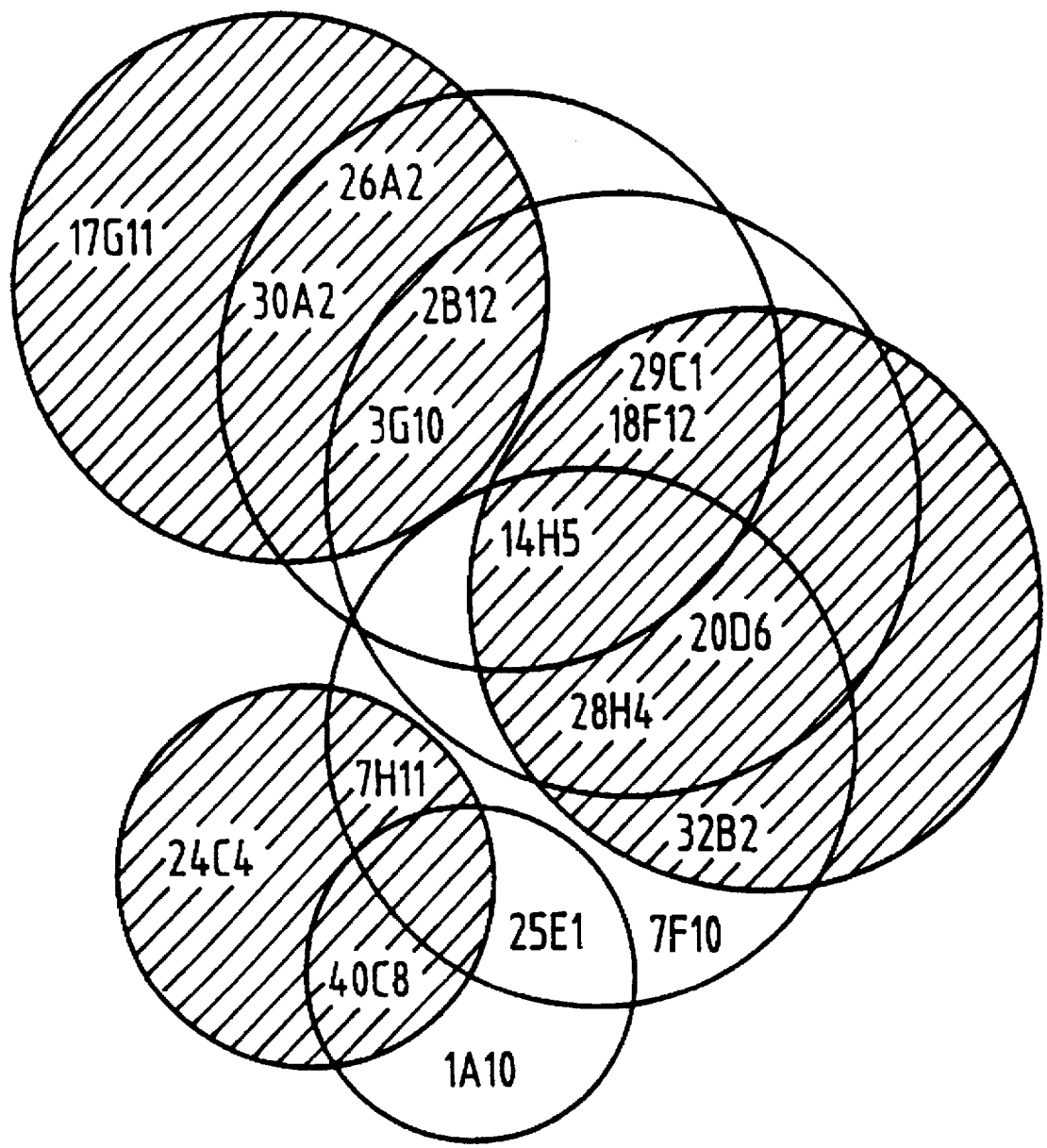
FIG. 2 is a schematic of the overlapping binding at monoclonal antibodies directed to the epitopes of the present invention.

The present invention thus relates to staphylokinase derivatives showing a reduced immunogenicity as compared to wild-type staphylokinase. The derivatives have essentially the amino acid sequence of wild-type staphylokinase or modified versions thereof, but at least one immunodominant epitope is eliminated without destroying the biological activity of the derivatives. In one embodiment of the invention the derivatives have essentially the amino acid sequence as depicted in FIG. 1 (SEQ ID NO: 2) in which one or more amino acids in one or more underlined clusters have been replaced by another amino acid thus destroying the corresponding epitope(s). Preferably the amino acids are replaced by alanine. By destroying the epitope(s) the reactivity of the derivatives with a monoclonal antibody panel directed to one or more of three epitope clusters I, II and III is reduced. This indicates that by replacing the wild-type amino acids with alanine the immunogenicity of staphylokinase is reduced.

The invention in particular relates to staphylokinase derivative M8 having the amino acid sequence as depicted in FIG. 1 in which the amino acids Lys on position 74, Glu on position 75 and Arg on position 77 in the underlined cluster 8 have been replaced by alanine thus destroying the corresponding epitope, to staphylokinase derivatives M3 having the amino acid sequence as depicted in FIG. 1 (SEQ ID NO:2) in which the amino acids Lys on position 35 and Glu on position 38 in the underlined cluster 3 have been replaced by alanine thus destroying the corresponding epitope, to staphylokinase derivative M9 having the amino acid sequence as depicted in FIG. 1 (SEQ ID NO:2) in which the amino acids Glu on position 80 and Asp on position 82in the underlined cluster 9 have been replaced by alanine thus destroying the corresponding epitope, and to staphylokinase derivative M3.8 having the amino acid sequence as depicted in FIG. 1 (SEQ ID NO: ) in which the amino acids Lys on position 35, Glu on position 38, Lys on position 74, Glu on position 75 and Arg on position 77 in the underlined clusters 3 and 8 have been replaced by alanine thus destroying the corresponding epitope. M3.8 is a double mutant having two epitopes destroyed.

The invention demonstrates that engineered variants of staphylokinase with reduced immunogenicity can be practical alternative thrombolytic agents to streptokinase or wild-type staphylokinase.

The invention also relates to a method for producing the derivatives of the invention by preparing a DNA fragment comprising at least the part of the coding sequence of staphylokinase that provides for its biological activity; performing in vitro site-directed mutagenesis on the DNA fragment to replace one or more codons, for wild-type amino acids by a codon for another amino acid; cloning the mutated DNA fragment in a suitable vector; transforming or transfecting a suitable host cell with the vector; and culturing the host cell under conditions suitable for expressing the DNA fragment. Preferably the DNA fragment is a 466 bp EcoRI-HindIII fragment of the plasmid pMEX602SAK, the in vitro site-directed mutagenesis is performed by an oligonucleotide-directed mutagenesis system using the plasmid pMa/c and the repair deficient *E. coli* strain WK6MutS, and the mutated DNA fragment is cloned in *E. coli* strain WK6.

The invention also relates to pharmaceutical compositions comprising at least one of the staphylokinase derivatives according to the invention together with a suitable excipient, for treatment of arterial thrombosis. Pharmaceutical compositions, containing less immunogenic staphylokinase variants as the active ingredient, for treating arterial thrombosis in human or veterinary practice may take the form of powders or solutions and may be used for intravenous or intraarterial administration. Such compositions may be prepared by combining (e.g. mixing, dissolving etc.) the active compound with pharmaceutically acceptable excipients of neutral character (such as aqueous or non-aqueous solvents, stabilizers, emulsifiers, detergents, additives), and further, if necessary with dyes. The concentration of the active ingredient in a therapeutical composition may vary widely between 0,1% and 100%, dependent on the character of the disease and the mode of administration. Further the dose of the active ingredient to be administered may vary between 0,05 mg and 1,0 mg per kg of body weight.

Furthermore the invention relates to the use of the staphylokinase derivatives for the treatment of arterial thrombosis, in particular myocardial infarction, and to the use of staphylokinase derivatives for the preparation of a pharmaceutical composition for the treatment of arterial thrombosis, in particular myocardial infarction.

In the above and the following the terms "derivatives" and "variants" are used interchangeably.

The present invention will be demonstrated in more detail in the following examples, that are however not intended to be limiting to the scope of the invention. Based on the present invention several variants and improvements will be obvious for the person skilled in the art. Thus random mutagenesis starting from the combination mutant 3.8 is likely to generate alternative mutants with reduced immunogenicity and possibly increased function activity, whereas alternative mutagenesis in the epitope neutralizing clusters will yield old variants with reduced immunogenicity.

EXAMPLE 1

Epitope Mapping of Wild-Type Staphylokinase

The epitope specificity of a panel of 17 murine monoclonal antibodies raised against wild-type staphylokinase (SakSTAR variant) was determined by real-time biospecific interaction analysis (BIA) using the BIAcore™ instrument (Pharmacia, Biosensor AB, Uppsala, Sweden). Monoclonal antibodies against SakSTAR were produced essentially by the method of Galfré and Milstein (30). BALB/c mice were immunized by subcutaneous injection of 10 µg SakSTAR in complete Freund's adjuvant, which was followed 2 weeks later by intraperitoneal injection of 10 µg SakSTAR in incomplete Freund's adjuvant. After an interval of at least 6 weeks, the mice were boosted intraperitoneally with 10 µg SakSTAR in saline on days 4 and 2 before the cell fusion. Spleen cells were isolated and fused with P3X63-Ag.8-6.5.3 myeloma cells (obtained from Dr. O. Schönherr, Organon, Oss, The Netherlands) according to Fazekas de St. Groth and Scheidegger (31). After selection in hypoxanthine, aminopterin, thymidine medium, the supernatants were screened for specific antibody production with a one-site noncompetitive micro-ELISA using microtiter plates coated with staphylokinase. The bound immunoglobulins were detected with horseradish peroxidase (HP)-conjugated rabbit anti-mouse IgG (32). Positive clones were used for the production of ascitic fluid in pristane-primed BALB/c mice (33). The IgG fraction of the monoclonal antibodies was purified from ascites by affinity chromatography on Protein A-Sepharose (34).

This biospecific interaction analysis technique, based on surface plasmon resonance (SPR) allows direct measurement of interactions in real time without the use of labels (35). Staphylokinase (SakSTAR) was immobilized on the surface of Sensor Chip CM5 using the Amine Coupling kit (Pharmacia Biosensor AB), as recommended by the manufacturer. This procedure links primary amino groups in the ligand to the carboxymethylated dextran surface of the Sensor Chip (36). Immobilization was performed from protein solutions at a concentration of 10 µg/ml in 10 mM Na-acetate at pH 5.0, at a flow of 5 µl/min during 6 min. This resulted in covalent attachment of 1,000–1,500 RU (resonance units) of staphylokinase moieties (corresponding to approximately 0.07 pmole/mm$^2$) (37). The second interacting component (the analyte: i.e. monoclonal antibody) was injected in solution over the sensor. The concentration of free analyte was kept constant through a continuous flow of solution at 20° C. past the sensor surface. At least four concentrations of each analyte (range 0–400 nM or 0–50 µM) in 10 MM HEPES, 3.4 nM EDTA, 0.15M NaCl and 0.005% Surfactant P20, pH 7.2, were injected at a flow rate of 5 µl/min during 6 in the association phase. Then sample was replaced by buffer, also at a flow rate of 5 µl/min during 6 o 30 min. After each cycle, the surface of the sensor chip was regenerated by injection of 3 µl of 15 mM HCl. Association ($k_{ass}$) and dissociation ($k_{diss}$) rate constants were derived from the sensorgrams as described in detail elsewhere (38). The equilibrium association consists ($K_A$), calculated as the ration of $k_{ass}$ and $k_{diss}$, for the binding to wild-type staphylokinase of the panel of 17 monoclonal antibodies studied, ranged between 0.6 and >25×10$^9$ M$^{-1}$ (median value 10$^{10}$ M$^{-1}$) (Table 1).

In table 1 the column indicated with "ID" states the various staphylokinase derivatives. Indications "17G11" "26A2" etc. refer to monoclonal antibodies binding to the indicated epitope clusters I, II and III. In the column "variants" the mutated amino acids and their position are indicated in the one letter code for amino acids. Epitope cluster I is recognized by the antibodies 17G11, 26A2, 30A2, 2B12 and 3G10, whereas epitope cluster II is recognized by the antibodies 29C1, 18F12, 14H5, 28H4, 20D6, 32B2 and 7F10, and epitope cluster III by the antibodies 7H11, 25E1, 40C8, 24C4 and 1A10. Deposit of certain of these hybridomas have been made in the Belgian Coordinated Collections of Microorganisms (BCCM), Laboratorium voor Moleculaire Biologie—Plasmidencollectie (LMBP), Universiteit Gent, K. L. Ledeganckstraat 35, B-9000 Gent, Belgium. The accession numbers for the hybridomas are as follows: 28H4, LMBP1629CB; 18F12, LMBP1628CB; 3G10, LMBP1632CB; 30A2, LMBP1630CB; 17G11, LMBP1635CB; 1A10, LMBP1634CB; 24C4, LMBP1633CB; 7H11, LMBP1627CB; and 32B2, LMBP1631CB.

Monoclonal antibodies directed against separate epitopes will bind independently of each other, whereas monoclonal antibodies directed against closely related epitopes will interfere with each other's binding. Therefore, the epitope specificity of a panel monoclonal antibodies is mostly easily determined by testing the ability of pairs of monoclonal antibodies to bind simultaneously to the antigen. Real-time biospecific interaction analysis (BIA) can be used to measure competitive binding of pairs of monoclonal antibodies to staphylokinase linked to the sensor chip surface. The analysis was carried out as described in Application Note 101 (Pharmacia Biosensor AB). Pair-wise binding tests divide the 17 monoclonal antibodies into 3 groups representing 3 non-overlapping epitopes on the antigen, as illustrated in FIG. 2. The independence of these epitopes was confirmed by the direct demonstration of additive binding of the monoclonal antibodies 26A2, 28H4 and 24C1. The antibodies were aligned according to their epitope specificity as illustrated in Table 1.

EXAMPLE 2

Construction and Epitope Mapping of "Charge-cluster to Alanine" Variants of Staphylokinase In the "charge-cluster to alanine" scan, clusters of hydrophilic charged amino acids were targeted. Staphylokinase (SakSTAR) contains 45 charged amino acids (2 His, 14 Glu, 8 Asp, 1 Arg and 20 Lys). These charged residues were mutagenized to Ala in clusters of one to four amino acids, as summarized in FIG. 1 (SEQ ID NO:2). A total of 22 mutants in which the underlined charged amino acids were replaced by alanine were designed. The amino acids that are to be replaced by alanine are indicated with a small vertical line within the cluster.

Mutants were prepared by site-directed mutagenesis and expressed in E. coli as detailed below. Restriction enzymes were purchased from Pharmacia, Uppsala, Sweden or Boehringer Mannheim (Mannheim, Germany). T4 DNA ligase, Klenow Fragment of E. coli DNA polymerase I and alkaline phosphatase were obtained from Boehringer Mannheim. The oligonucleotide-directed mutagenesis system and the pMa/c plasmids were kindly provided by Corvas (Ghent, Belgium) (39). The expression vector pMEX602SAK was kindly provided by the Institut für Molekulare Biotechnologie, Jena, Germany (25). M123KO7 helper phage was purchased form Promega (Leiden, The Netherlands). Luria Broth growth medium was purchased from Lift Technologies (Merelbeke, Belgium). Plasminogen was purified from human plasma as described elsewhere (40).

Enzyme reactions were performed using the conditions suggested by the suppliers. Plasmid DNA was isolated using a QIAGEN-purification protocol (provided by Westburg, Leusden, The Netherlands). Transformations of *E. coli* were performed utilizing the calcium phosphate procedure. DNA sequencing was performed using the dideoxy chain termination reaction method and the Automated Laser fluorescent A.L.F.™ (Pharmacia). Site directed mutagenesis for the mutants D5,K6 (M20) until K86,E88 (M10), was performed using the pMa/c, using the repair deficient *E. coli* strains WK6MutS. Propagation of the plasmids pMa/c or derivatives, preparation of single stranded DNA and expression was done in *E. coli* WK6 (39). The mutants D93,K94 (M11) until K134,K135,K136 (M19), were constructed in the Institut für Molekulare Biotechnologie as previously described (16). The chromogenic substrate (S2403) L-Pyroglutamyl-L-phenylalanyl-L-lysine-P-nitroanaline hydrochloride was purchased from Chromogenix. $^{125}$I-labeled fibrinogen was purchased from Amersham.

A 466-base pair EcoRI-HindIII fragment containing the entire coding region for SakSTAR was cut out of the plasmid pMEX602SAK and cloned into the EcoRI-HindIII sites of the pMa/c plasmid lacking the promoter sequence (pMa/c-STAR). For in vitro site-directed mutagenesis, single stranded DNA of this construct was prepared by transformation of the pMc-STAR construct in *E. coli* and injection of an overnight culture with helper phage M13KO7. Four hours after injection, cells were isolated from the medium by PEG-precipitation and phenol-chloroform extraction. Subsequently, single stranded pMa/c-STAR was hybridized with single stranded pMc/a (EcoRI-HindIII) vector DNA and the appropriate 40 to 50 base synthetic oligonucleotide. Extension reactions were carried out with the Klenow fragment of DNA polymerase as described. After transformation of *E. coli* WK6MutS and selection on ampicillin, colonies were grown on nitrocellulose membranes, denatured in situ and DNA was hybridized overnight at room temperature using the respective radiolabeled mutant oligonucleotides (1.5×10$^8$ cpm of [γ$^{32}$P]-ATP used for T4 polynucleotide kinase labeling of 20–30 ng of oligonuleotide). Filters were washed at 42° C. using solutions containing 0.1% SDS and 2× SSC, 0.2× SSC, 0.1× SSC. Plasmid DNA was extracted from 10 ml bacterial cultures from each positive clone and analyzed by restriction enzyme digestion. The desired mutations were confirmed by sequencing of the complete coding sequence using A.L.F.™.

The mutated HindIII-EcoRI fragment was then ligated back into the pMEXSAK602 expression vector containing the pTag promoter (39). The mutant proteins were produced intracellularly and in soluble form in *E. coli* WK6 cells transformed with this vector. The mutants were purified from the sonicated bacterial extracts using cation exchange and hydrophobic interaction chromatography (25).

SakSTAR mutants were obtained with yields ranging between 10 and 80 mg/l, representing recoveries of 15 to 88% of the starting material. The purified material was pure as shown by electrophoresis on non reduced 10–15% gradient gels (not shown). NH$_2$-terminal amino acid analysis confirmed the Ser-Ser-Ser-Phe-Asp (SEQ ID NO:1) sequence of mature staphylokinase. A more detailed biochemical characterization of these staphylokinase mutants will be reported elsewhere (41).

Protein concentrations ere determined according to Bradford (42). The fibrinolytic activities of SakSTAR solutions were determined with a chromogenic substrate assay carried out in microtiters plates using a mixture of 80 μl SakSTAR solution and 100 μl Glu-plasminogen solution (final concentration 0.5 mM). After incubation for 30 min at 37° C., generated plasmin was quantitated by addition of 30 μl S2403 (final concentration 1 μM) and measurement of the absorption at 405 nm. The activity was expressed in home units (HU) by comparison with an in-house standard (lot STAN5) which was assigned an activity of 100,00 HU per mg protein as determined by amino acid composition (11). SDS-PAGE was performed with the Phast System™ (Pharmacia, Uppsala, Sweden) using 10–15% gradient gels and Coomassie Brilliant blue staining. Reduction of the sample was performed by heating at 100° C. for 3 min in the presence of 1% SDS and 1% dithioerythritol.

The fibrinolytic activities of the different SakSTAR mutants determined with the chromogenic substrate assay and the clot lysis assay are summarized in table 1.

Of the 22 mutants, designed as illustrated in FIG. 1, K57,E58,K59 (M5), E99,E100,E102 (M14) and D5,K6 (M20) could not be obtained in purified form, whereas K11,D13,D14 (M1), E46,K50 (M4) and E65,D69 (M7) were inactive. Thirteen mutants, summarized in Table 1 were studied in detail, together with wild-type SakSTAR. Of these mutants K8,K10 (M21), D33,K35 (M2), E61,E65 (M6), K86,E88 (M10), D93,K94 (M11), K96,K97,K98 (M12), E108,E109 (M15), D115,E118,H119 (M16), H119,K121 (M17) and E135,K136,K137 (M19) reacted with the monoclonal antibody panel is a similar way as SakSTAR. However K35,E38 (M3) and E80,D82 (M9) reacted poorly with the antibody cluster 7H11, 25E1, 40C8, whereas K74,E75, R77 (M8) reacted poorly with the cluster 26A2, 30A2, 2B12 and 3G10. Additivity of epitope elimination was established with the mutant K35,E38/K74,E75,R77 (M3.8) which combined the reduced reactivity with the monoclonal antibodies of both parent molecules.

EXAMPLE 3

Adsorption with Wild-Type and "Charge-Cluster to Alanine" Staphylokinase Variants of Antibodies, Elicited in Patients by Treatment with SakSTAR In order to obtain information on the epitope specificity of induced antibodies elicited in patients with acute myocardial infarction after treatment with SakSTAR plasma samples from 7 patients were absorbed with a two-fold molar excess (over the staphylokinase neutralizing activity) of single and combined "charge-cluster to alanine" mutants for 10 minutes before determination of residual binding to SakSTAR by biospecific interaction analysis. The staphylokinase-neutralizing activity in these samples was determined as described elsewhere (23). The results were summarized in Table 2. Whereas the wild-type SakSTAR absorbed more than 90 percent of the binding antibodies from all samples, incomplete absorption (50 to 90 percent) was observed with mutant K35,E38 (M3) in 2 patients, and with mutant K74, E75,R77 (M8) in 5 patients (median value of 63 percent for the 7 patients). Absorption with the combination mutant K35,E38,K74,E75,R77 (M3.8) removed less than 50% of the antibodies in 3 patients (median value of 51 percent for the 7 patients), whereas, as anticipated, a mixture of the parent molecules of the combination mutant (M3 and M8) consistently absorbed in excess of 90 percent of the antibodies.

EXAMPLE 4

Immunogenicity of "Charge-Cluster to Alanine" Variants of Staphylokinase in Rabbits Immunized With Wild-Type Staphylokinase (SakSTAR), With Mutant K74,E75,R77 (M8), and With the Combination Mutant K35,E38/K74,E75,R77 (M3.8)

The comparative immunogenicity of SakSTAR versus the mutant K74,E75,R77 (M8) which absorbed a median of 63 percent of the antibodies elicited in 7 patients treated with SakSTAR, or of SakSTAR versus the combination mutant K35,E38/K74,E75,R77 (M3.8) which only absorbed a median of 31 percent of the antibodies elicited in these 7 patients (cfr. Example 3) was studied in groups of up to 8 rabbits. The immunogenicity was quantitated at 6 weeks by determination of the staphylokinase-neutralizing activity in plasma and the residual thrombolytic potency, essentially as previously described (23).

Briefly, staphylokinase-neutralizing activity in plasma was determined by adding increasing concentrations of wild-type or mutant SakSTAR (50 μl volumes containing 0.2 to 1000 μg/ml) to a mixture of 300 μl citrated human plasma and 50 μl buffer or rabbit plasma, immediately followed by addition of 100 μl of a mixture containing thrombin (50 NIH units/ml) and $CaCl_2$ (25 mM). The plasma clot lysis time was measured and plotted against the concentration of SakSTAR or M8. From this curve the concentration of plasminogen activator that produced complete clot lysis in 20 min was determined. The neutralizing activity titer was determined as the difference between the rabbit plasma and buffer values and was expressed in μg per ml rabbit plasma.

The thrombolytic properties were studied using 0.3 ml $^{125}$I-fibrin labeled platelet-poor rabbit plasma clots, inserted into an extracorporeal arteriovenous loop. An exposed femoral artery was therefore catheterized with a 4 French catheter (Portex White, Portex, Hythe, UK) and connected via two hypodermic syringes to a catheterized ear vein. The blood flow through the extracorporeal loop was maintained at 10 ml/min with a peristaltic pump. $^{125}$I-fibrin labeled plasma clots were introduced in each of two syringes inserted in the loop. The plasma clots were prepared by mixing 0.3 ml platelet-poor plasma with a trace amount (approximately 1.5 μCi) $^{125}$I-labeled human fibrinogen solution (Amersham, Buckinghamshire, UK) and 0.07 ml of a mixture of bovine thrombin (15 NIH units/ml) and 0.5M $CaCl_2$, followed by incubation for 30 min at 37° C. Thirty min before the start of the infusion, 7.5 mg/kg ridogrel (a combined thromboxane synthase inhibitor and prostaglandin endoperoxide receptor antagonist) (43) was administered as an intravenous bolus to prevent platelet deposition in the extracorporeal loop. The animals were anticoagulated with heparin (300 units/kg followed by a continuous infusion of 200 units/kg/h throughout the experiment) and randomly allocated to infusion with 400 μg/kg SakSTAR, 1000 μg/kg M8 or 1,000 μg/kg M3.8. The thrombolytic agents were given intravenously as a 10% bolus and a 90% infusion over 1 h. The time course of clot lysis was monitored continuously by external gamma counting, using two 3×0.5 inch sodium iodide/thallium crystals (Bicron, Newbury Ohio) positioned over the extracorporeal loops. The scintillation crystals were connected to a dedicated Canberra-S100 system (Canberra-Packard, Meriden, Conn.), and the data were analyzed as described elsewhere (44). At the end of the experiment the residual clots were also recovered from the syringes for determination of their radioisotope content. The animal experiments were conducted conform the guiding principles of the American Physiological Society and the International Committee on Thrombosis and Haemostasis (45).

The results (mean ±SD) are summarized in Table 3. In 8 rabbits assigned to the SakSTAR group the baseline neutralizing activity in plasma was 0.9±6.0 μg/ml against SakSTAR and 0.6±0.3 μg/ml against M8. Intravenous infusion 400 μg/kg SakSTAR produced 68±18 percent lysis. These rabbits were then immunized subcutaneously with 400 μg SakSTAR suspended in complete Freund adjuvant at week 2 and with the same amount in incomplete Freund adjuvant at week 3 and 5. At week 6 the plasma neutralizing activity was increased to 59±47 μg/ml against SakSTAR and to 22±16 μg/ml against M8 whereas the residual thrombolytic potency of 400 μg/kg SakSTAR had decreased to 7.5±2.7 percent and of 1,000 μg/kg M8 to 4.1±4.8 percent. In 8 rabbits assigned to the M8 group, the baseline neutralizing activity in plasma was 1.4±0.2 μg/ml against SakSTAR and 0.6±0.5 μg/ml against M8. Intravenous infusion of 1000 μg/kg M8 produced 41±13 percent lysis. These rabbits were then immunized with 400 μg M8 suspended in complete Freund adjuvant at week 2 land with the same amount in incomplete Freund adjuvant at weeks 3 and 5. At week 6 the plasma neutralizing activity was increased to 3.8±1.8 μg/ml against SakSTAR and to 5.9±2.7 μg/ml against M8. Infusion of 400 μg/kg SakSTAR in four of these rabbits produced 49±28 percent clot lysis whereas infusion of 1000 μg/kg M8 in the four other rabbits produced 24±11 percent lysis. These results show that in this directly comparative study of SakSTAR and M8, the latter induces less staphylokinase neutralizing activity and resistance to lysis than the former.

In 4 additional rabbits assigned to immunization with SakSTAR, the baseline neutralizing activity in plasma was 0.9±0.4 μg/ml against SakSTAR and 0.7±0.4 μg/ml against M3.8. Intravenous infusion of 400 μg/kg SakSTAR produced 79±8.4 percent clot lysis. After immunization as described above, the plasma neutralizing activity at 6 weeks was increased to 21±22 μg/ml against SakSTAR and to 21±22 against M3.8. Intravenous infusion of 1,000 μg/ml M3.8 produced 53±13 percent clot lysis. After immunization as described above the plasma neutralizing activity at 6 weeks was 2.0±0.8 μg/ml against SakSTAR and 8.0±2.3 μg/ml against M3.8, whereas the residual thrombolytic potency of 400 μg/ml SakSTAR was 89±17 percent and that of 1,000 μg/ml M3.8 was 80±15 percent. These results show that compared with SakSTAR, M3.8 is much less immunogenic, maintaining its full thrombolytic capacity in rabbits after an immunization schedule which, when carried out with SakSTAR, produced virtual refractoriness to lysis and, when carried out with M8, produced partial resistance to lysis.

The invention thus provides new staphylokinase derivatives with a reduced immunogenicity as compared to wild-type staphylokinase. The repeated use of these new variants will induce a much lower immune response than the use of wild-type staphylokinase.

TABLE 1

Equilibrium association constants ($K_A \times 10^9$ M$^{-1}$) for the binding of murine monoclonal antibodies to wild-type and "charge cluster to alanine" mutants of staphylokinase.

| ID | Variant | Spec. Act. ($\times 10^3$/mg) | Epitope cluster I | | | | | Epitope cluster II | | | | | | |
|---|---|---|---|---|---|---|---|---|---|---|---|---|---|---|
| | | | 17G11 | 2GA2 | 30A2 | 2B12 | 3G10 | 29C1 | 18F12 | 14H5 | 28H4 | 20D6 | 32B2 | 7F10 |
| | SakSTAR | 130 | 6.4 | 17 | 7.4 | 19 | 35 | >9.2 | >18 | >25 | >18 | 2.9 | >14 | 1.1 |
| M21 | K8, K10 | 24 | — | 16 | — | 29 | — | — | 22 | — | 26 | — | 18 | — |
| M2 | D33, K35 | 125 | 2.1 | 19 | — | 14 | 19 | 8.7 | 15 | — | 32 | — | 10 | 5.3 |
| M3 | K35, E38 | 97 | 18 | 11 | 5.7 | >14 | 9.5 | 8.1 | 6 | 10 | 8.5 | 0.018 | >9.2 | >7.6 |
| M6 | E61, E65 | 80 | 9.5 | >10 | 8.8 | 21 | 29 | >4.5 | >11 | >16 | 6.6 | 2.6 | >7.2 | 4.6 |
| M8 | K74, E75, R77 | 110 | >23 | 0.2 | 0.22 | 0.41 | 0.24 | >12 | >20 | >25 | >21 | 4.7 | >16 | 1.7 |
| M9 | E80, D82 | 130 | 15 | 13 | 10 | 21 | 28 | 18 | 4.7 | >25 | >20 | 3.5 | >20 | 1.9 |
| M10 | K86, E88 | 73 | 7.2 | 1.4 | 3.7 | 6 | 4.6 | 5.9 | 5.7 | 4.9 | 7.7 | 8.2 | 15 | 4.4 |
| M11 | D93, K94 | 97 | — | 19 | — | 30 | — | — | 18 | — | >10 | — | 9 | — |
| M12 | K96, K97, K98 | 47 | — | 41 | — | 37 | — | — | >16 | — | 19 | — | 16 | — |
| M15 | E108, K109 | 170 | — | 5.1 | — | 19 | — | — | 28 | — | 21 | — | 21 | — |
| M16 | D115, E118, H119 | 32 | — | 32 | — | 21 | — | — | 13 | — | 23 | — | 9.3 | — |
| M17 | H119, K121 | 130 | — | 24 | — | 26 | — | — | 25 | — | 29 | — | 12 | — |
| M19 | E134, K135, K136 | 74 | 22 | 21 | 6.7 | 25 | 25 | >6.5 | >18 | >25 | >15 | 4 | >12 | 1.7 |
| M3.8 | K35, E38/K74, E75, R77 | 35 | 0.71 | 0.05 | | 0.09 | 0.07 | 8.5 | 5.8 | | 6.7 | — | 6.8 | 0.04 |

| ID | Variant | Spec. Act. ($\times 10^3$/mg) | Epitope cluster III | | | | |
|---|---|---|---|---|---|---|---|
| | | | 7H11 | 25E1 | 40C8 | 24C4 | 1A10 |
| | SakSTAR | 130 | 0.6 | 11 | 1.6 | 6.3 | 2.0 |
| M21 | K8, K10 | 24 | — | 11 | — | 18 | — |
| M2 | D33, K35 | 125 | — | 5.1 | 3.8 | 5.1 | 3.0 |
| M3 | K35, E38 | 97 | 0.02 | 0.05 | 0.15 | 6.1 | 2.6 |
| M6 | E61, E65 | 80 | 0.51 | 4.6 | 2 | 5.9 | 1.5 |
| M8 | K74, E75, R77 | 0.33 | 15 | 1.2 | >6.6 | 3.1 | |
| M9 | E80, D82 | 130 | 0.03 | 0.07 | 0.05 | ≤0.01 | 1.2 |
| M10 | K86, E88 | 73 | 0.09 | 5.4 | 0.8 | 1.9 | 0.13 |
| M11 | D93, K94 | 97 | — | 11 | — | 7 | — |
| M12 | K96, K97, K98 | 47 | — | 17 | — | 13 | — |
| M15 | E108, K109 | 170 | — | 6.9 | — | 10 | — |
| M16 | D115, E118, H119 | 32 | — | 24 | — | 9 | — |
| M17 | H119, K121 | 130 | — | 11 | — | 20 | — |
| M19 | E134, K135, K136 | 74 | 0.2 | 11 | 0.94 | 6 | |
| M3.8 | K35, E38/K74, E75, R77 | 35 | 0.06 | — | 0.05 | 1.9 | 0.08 |

Association constants ≧ 10-fold lower than those of wild-type SakSTAR are underlined.

TABLE 2

Absorption of antibodies, elicited by treatment with wild-type staphyloidnase (SakSTAR) in patients with acute myocardinal infarction, with wild-type and "charge-cluster to alanine" staphylokinase variants.

| ID | Titer (µg/ml) | Percent antibodies absorbed with | | | |
|---|---|---|---|---|---|
| | | SakSTAR | M3 | M8 | M38 | M3 + M8 |
| COEL | 26 | + | + | 63 | 51 | + |
| BANC | 11 | + | 68 | 59 | 42 | + |
| FLUS | 12 | + | + | 60 | 42 | + |
| VERS | 75 | + | + | + | + | + |
| DEBE | 11 | + | + | 47 | 40 | + |
| VERM | 45 | + | 89 | 64 | 64 | + |
| VERB | 18 | + | + | + | + | + |
| Epitope cluster missing | 0 | III | I | I + III | 0 | |

Absorption of ≧ 90 percent is represented as +.
The epitope clusters are as identified in Tables I and II.

TABLE 3

Immunogenicity of SakSTAR and M8 in rabbits

| Immunizing agent | Neutralizing activity (µmg/ml) | | | | | | Clot lysis (percent) | | | | | |
|---|---|---|---|---|---|---|---|---|---|---|---|---|
| | SakSTAR | | | M8 | | | SakSTAR | | | M8 | | |
| | baseline | 6 weeks | p | baseline | 6 weeks | p | baseline | 6 weeks | p | baseline | 6 weeks | p |
| SakSTAR | 0.9 ± 0.6(8) | 59 ± 47(8) | 0.01 | 0.6 ± 0.3(8) | 22 ± 16(8) | 0.01 | 68 ± 18(8) | 7.5 ± 2.4(4) | 0.001 | — | 4.1 ± 4.8(4) | — |
| M8 | 1.4 ± 0.2(8) | 3.8 ± 1.8(8) | 0.01 | 0.6 ± 0.5(8) | 5.9 ± 2.7(8) | 0.005 | — | 49 ± 28(4) | — | 41 ± 13(8) | 24 ± 11(4) | 0.03 |
| p | 0.04 | 0.005 | | 1.0 | 0.01 | | — | 0.001 | | — | 0.02 | |

REFERENCES

1. Collen D: On the regulation and control of fibrinolysis. Edward Kowalski Memorial Lecture, Thromb Haemostas 43: 77–79, 1980
2. Collen D: Lijnen H R: Basis and clinical aspects of fibrinolysis and thrombolysis. Blood 78: 3114–3124, 1991
3. Collen D, Van de Werf F: Coronary thrombolysis with recombinant staphylokinase in patients with evolving myocardial infarction. Circulation 87: 1850–1853, 1993
4. Vanderschueren S, Collen D: Immunogeniciteit van streptokinase en implicaties voor gebruik. Tijdschr Geneesk 50: 1639–1644, 1994.
5. Lack C H: Staphylokinase: an activator of plasma protease. Nature 161: 559, 1948
6. Lewis J H, Ferguson J H: A proteolytic enzyme system of the blood. III. Activation of dog serum profibrinolysin by staphylokinase. Am J Physiol 166: 594, 1951
7. Winkler K C, DeWaart J, Grootsen C, Zegers B J M, Tellier N F, Vertegt C D: Lysogenic conversion of staphylococci to loss of beta-toxin. J Gen Microbiol 39: 321, 1965
8. Collen D, Lijnen H R. Staphylokinase, a fibrin-specific plasminogen activator with therapeutic potential ? Blood 84: 680–686, 1994.
9. Sako T, Sawaki S, Sakurai T, Ito S, Yoshizawa Y, Kondo I: Cloning and expression of the staphylokinase gene of *Staphylococcus aureus* in *Escherichia coli*. Molec Gen Genet 190: 271–277, 1983
10. Behnke D, Gerlach D; Cloning and expression in *Escherichia coli, Bacillus subtilis,* and *Streptococcus sanguis* of a gene for staphylokinase—a bacterial plasminogen activator. Molec Gen Genet 210: 528–534, 1987
11. Collen D, Silence K, Demarsin E, De Mol M, Lijnen H R: Isolation and characterization of natural and recombinant staphylokinase. Fibrinolysis 6: 203–213, 1992
12. Sako T: Overproduction of staphylokinase in *Escherichia coli* and its characterization. Eur J Biochem 149: 557–563, 1985
13. Gerlach D, Kraft R, Behnke D: Purification and characterization of the bacterial plasminogen activator staphylokinase secreted by a recombinant *Bacillus subtilis*. Zbl Bakt Mikr Hyg 269: 314–322 1988
14. Sako T, Tsuchida N: Nucleotide sequence of the staphylokinase gene from *Staphylococcus aureus*. Nucleic Acids Res 11: 7679–7693, 1983
15. Collen D, Zhao Z A, Holvoet P, Marynen P: Primary structure and gene structure of staphylokinase. Fibrinolysis 6: 226–231, 1992
16. Schlott B, Hartmann M, Gührs K H, Birch-Hirschfeld , Gase A, Vetterman S, Collen D, Lijnen H R: Functional properties of recombinant staphylokinase variants obtained by site-specific mutagenesis of methionine-26. Biochim Biophys Acta 1204: 235–242, 1994
17. Sakai M, Watanuki M, Matsuo O: Mechanism of fibrin-specific fibrinolysis by staphylokinase: participation of $\alpha_2$-plasmin inhibitor. Biochem Biophys Res Comm 162: 830–837, 1989
18. Matsuo O, Okada K, Fukao H, Tomicka Y, Ueshima S, Watanuki M, Sakai M: Thrombolytic properties of staphylokinase. Blood 76: 925–929, 1990
19. Lijnen H R, Van Hoef B, De Cock F, Okada K, Ueshima S, Matsuo O, Collen D: On the mechanism of fibrin-specific plasminogen activation by staphylokinase. J Biol Chem 266: 11826–11832, 1991
20. Lijnen H R, Van Hoeft B, Matsuo O, Collen D: On the molecular interactions between plasminogen-staphylokinase, $\alpha_2$-antiplasmin and fibrin. Biochim Biophys Acta 1118: 144–148, 1992
21. Silence K, Collen D, Lijnen H R: Interaction between staphylokinase, plasmin(ogen) and $\alpha_2$-antiplasmin. Recycling of staphylokinase after neutralization of the plasmin-staphylokinase complex by $\alpha_2$-antiplasmin. J Biol Chem 268: 9811–9816, 1993
22. Silence K, Collen D, Lijnen H R: Regulation by $\alpha_2$-antiplasmin and fibrin of the activation of plasminogen with recombinant staphylokinase in plasma. Blood 82: 1175–1183, 1993
23. Collen, D, De Cock F. Vanlinthout I, Declerck P J, Lijnen H R, Stassen J M: Comparative thrombolytic and immunogenic properties of staphylokinase and streptokinase. Fibrinolysis 6: 232–242, 1992
24. Collen D, De Cock F, Stassen J M: Comparative immunogenicity and thrombolytic properties toward arterial and venous thrombi of streptokinase and recombinant staphylokinase in baboons. Circulation 87: 996–1006, 1993
25. Schlott B, Hartmann M, Gührs K H, Birch-Hirschfeid E. Pohl H D. Vanderschueren S, Van de Werf F, Michoel A, Collen D, Behnke D: High yield production and purification of recombinant staphylokinase for thrombolytic therapy. Bio/technology 12: 185–189, 1994
26. Declerck P J, Vanderschueren S, Billiet J, Moreau H, Collen D: Prevalence and induction of circulating antibodies against recombinant staphylokinase. Thromb Haemostas 71: 129–133, 1994
27. Vanderschueren S M F, Stassen J M, Collen D: On the immunogenicity of recombinant staphylokinase in patients and in animal models. Thromb Haemostas 72: 297–301, 1994
28. White H: Thrombolytic treatment for recurrent myocardial infarction. Br Med J 302: 429–430, 1991
29. Gase A, Hartmann M, Schlott B, Röcker A, Gührs K H: (Personal communication)
30. Galfré G, Milstein C: Preparation of monoclonal antibodies: strategies and procedures. Methods Enzymol 73: 3–46, 1981.

31. de St. Groth S F, Scheidegger D: Production of monoclonal antibodies: strategies and tactics. J Immunol Methods 35: 1–21, 1980
32. Nakane P K, Kawaoi A: Peroxidase-labeled antibody. A new method for conjugation. J Histochem Cytochem 22: 1084–1091, 1974
33. Anderson N, Potter M: Induction of plasma cell tumours in Balb-c mice with 2, 6, 10, 14 tetramethylpentadecane (pristane). Nature 222: 994–995, 1969
34. Ey P L, Prowse S J, Jenkin C R: Isolation of pure $IgG_1$, $IgG_{2a}$ and $IgG_{2b}$ immunoglobulins from mouse serum using protein A-Sepharose. Immunochemistry 15: 429–436, 1978
35. Jönsson U, Malmqvist M: Real time biospecific interaction analysis. The integration of surface plasmon resonance detection, general biospecific interface chemistry and microfluidics into one analytical system. Adv Biosensors 2: 291–336, 1992
36. Johnsson B, Löfas S, Lindquist G: Immobilization of proteins to a carboxymethyldextran-modified gold surface for biospecific interaction analysis in surface plasmon resonance sensors. Anal Biochem 198: 268–277, 1991
37. BiAcore system manual, 5-2, Pharmacia Biosensor AB, Uppsala, Sweden
38. Karisson R, Michaelsson A, Mattsson L: Kinetic analysis of monoclonal antibody-antigen interactions with a new biosensor based analytical system. J Immunol Methods 145: 229–240, 1991
39. Stanssens P, Opsomer C, McKeown Y, Kramer W, Zabeau M, Friz M J: Efficient oligonucleotide-directed construction of mutations in expression vectors by the gapped duplex DNA method using alternating selectable markers. Nucleic Acids Res 17: 4441–4454, 1989
40. Deutsch D G, Mertz E T. Plasminogen: purification from human plasma by affinity chromatography. Science 170: 1095–1096, 1970
41. Silence K, Hartmann M, Gührs K H, Gase A, Schlott B, Collen D, Lijnen H R. Structure-function relationships in staphylokinase as revealed by "cluster-charge-to-alanine" mutagenesis (in preparation).
42. Bradford M M. A rapid and sensitive method for the quantitation of microgram quantities of protein utilizing the principle of protein-dye binding. Anal Biochem 72: 248, 1976.
43. De Clerck F, Beetens J, de Chaffoy de Courcelles D, Freyne E, Janssen P. A R68070: thromboxane A2 synthetase inhibition and thromboxane A2/prostaglandin endoperoxide receptor blockade combined in one molecule. 1. Biochemical profile in vitro. Thromb Haemost 61: 35–42, 1989.
44. Stassen J M, Vanlinthout I, Lijnen H R, Collen D. A hamster pulmonary embolism model for the evaluation of the thrombolytic and pharmacokinetic properties of thrombolytic agents. Fibrinolysis 4 (Suppl 2): 15–21, 1990.
45. Giles A R. Guidelines for the use of animals in biomedical research. Thromb Haemost 58:1078-14 1084, 1987.

---

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
( A ) LENGTH: 5
( B ) TYPE: AMINO ACID
( C ) STRANDEDNESS: SINGLE
( D ) TOPOLOGY: UNKNOWN ( x i ) SEQUENCE DESCRIPTION: SEQ ID NO: 1:

```
Ser  Ser  Ser  Phe  Asp
1                   5
```

( 2 ) INFORMATION FOR SEQ ID NO: 2:

( i ) SEQUENCE CHARACTERISTICS:
( A ) LENGTH: 136
( B ) TYPE: AMINO ACID
( C ) STRANDEDNESS: SINGLE
( D ) TOPOLOGY: UNKNOWN ( x i ) SEQUENCE DESCRIPTION: SEQ ID NO: 2:

```
Ser  Ser  Ser  Phe  Asp  Lys  Gly  Lys  Tyr  Lys  Lys  Gly  Asp  Asp
1                   5                        10
Ala  Ser  Tyr  Phe  Glu  Pro  Thr  Gly  Pro  Tyr  Leu  Met  Val  Asn
15                       20                       25
Val  Thr  Gly  Val  Asp  Ser  Lys  Gly  Asn  Glu  Leu  Leu  Ser  Pro
       30                      35                        40
His  Tyr  Val  Glu  Phe  Pro  Ile  Lys  Pro  Gly  Thr  Thr  Leu  Thr
            45                      50                        55
```

-continued

| | | | | | | | | | | | | | |
|---|---|---|---|---|---|---|---|---|---|---|---|---|---|
| Lys | Glu | Lys | Ile<br>60 | Glu | Tyr | Tyr | Val | Glu<br>65 | Trp | Ala | Leu | Asp | Ala<br>70 |
| Thr | Ala | Tyr | Lys | Glu<br>75 | Phe | Arg | Val | Val | Glu<br>80 | Leu | Asp | Pro | Ser |
| Ala<br>85 | Lys | Ile | Glu | Val | Thr<br>90 | Tyr | Tyr | Asp | Lys | Asn<br>95 | Lys | Lys | Lys |
| Glu | Glu<br>100 | Thr | Lys | Ser | Phe | Pro<br>105 | Ile | Thr | Glu | Lys | Gly<br>110 | Phe | Val |
| Val | Pro | Asp<br>115 | Leu | Ser | Glu | His | Ile<br>120 | Lys | Asn | Pro | Gly | Phe<br>125 | Asn |
| Leu | Ile | Thr | Lys<br>130 | Val | Val | Ile | Glu | Lys<br>135 | Lys | | | | |

I claim:

1. The staphylokinase derivative M8 having the amino acid sequence as depicted in FIG. 1 (SEQ ID NO: 2) in which the amino acids Lys at position 74, Glu at position 75 and Arg at position 77 in the underlined cluster 8 have been replaced by alanine thus destroying the corresponding epitope.

2. The staphylokinase derivative M3 having the amino acid sequence as depicted in FIG. 1 (SEQ ID NO: 2) in which the amino acids Lys at position 35 and Glu at position 38 in the underlined cluster 3 have been replaced by alanine thus destroying the corresponding epitope.

3. The staphylokinase derivative M9 having the amino acid sequence as depicted in FIG. 1 (SEQ ID NO: 2) in which the amino acids Glu at position 80 and Asp at position 82 in the underlined cluster 9 have been replaced by alanine thus destroying the corresponding epitope.

4. The staphylokinase derivative M3.8 having the amino acid sequence as depicted in FIG. 1 (SEQ ID NO: 2) in which the amino acids Lys at position 35, Glu at position 38, Lys at position 74, Glu at position 75 and Arg at position 77 in the underlined clusters 3 and 8 have been replaced by alanine thus destroying the corresponding epitope.

5. Staphylokinase derivative showing a reduced immunogenicity as compared to wild-type staphylokinase and the amino acid sequence as depicted in FIG. 1 (SEQ ID NO: 2) in which one or more amino acids in one or more clusters of amino acids selected from the group consisting of amino acids 5 and 6; 8 and 10; 11, 13 and 14; 22; 33 and 35; 35 and 38; 46 and 50; 57–59; 61 and 65; 65 and 69; 74, 75 and 77; 80 and 82; 86 and 88; 93 and 94; 96–98; 99 and 100; 99, 100 and 102; 108 and 109; 115. 118 and 119; 119 and 121; 130; and 134–136, have been replaced by another amino acid thus destroying the corresponding epitope(s).

6. The staphylokinase derivatives as claimed in claim 5 having the amino acid sequence as depicted in FIG. 1 (SEQ ID NO: 2) in which one or more amino acids in one or more clusters of amino acids selected from the group consisting of amino acids 5 and 6; 8 and 10; 11, 13 and 14; 22; 33 and 35; 35 and 38; 46 and 50; 57–59; 61 and 65; 65 and 69; 74, 75 and 77; 80 and 82; 86 and 88; 93 and 94; 96–98; 99 and 100; 99, 100 and 102; 108 and 109; 115, 118 and 119; 119 and 121; 130; and 134–136, have been replaced by alanine thus destroying the corresponding epitope(s).

7. The staphylokinase derivatives as claimed in claim 5 having the amino acid sequence as depicted in FIG. 1 (SEQ ID NO: 2) in which one or more amino acids in one or more clusters of amino acids selected from the group consisting of amino acids 5 and 6; 8 and 10; 11, 13 and 14; 22; 33 and 35; 35 and 38; 46 and 50; 57–59; 61 and 65; 65 and 69; 74, 75 and 77; 80 and 82; 86 and 88; 93 and 94; 96–98; 99 and 100; 99, 100 and 102; 108 and 109; 115, 118 and 119; 119 and 121; 130; and 134–136, have been replaced by alanine thus reducing the reactivity of the derivatives with a monoclonal antibody panel of antibodies 17G11, 30A2 and 3G10.

8. The staphylokinase derivatives as claimed in claim 5 having the amino acid sequence as depicted in FIG. 1 (SEQ ID NO: 2) in which one or more amino acids in one or more clusters of amino acids selected from the group consisting of amino acids 5 and 6; 8 and 10; 11, 13 and 14; 22; 33 and 35; 35 and 38; 46 and 50; 57–59; 61 and 65; 65 and 69; 74, 75 and 77; 80 and 82; 86 and 88; 93 and 94; 96–98; 99 and 100; 99, 100 and 102; 108 and 109; 115, 118 and 119; 119 and 121; 130; and 134–136, have been replaced by alanine thus reducing the reactivity of the derivatives with a monoclonal antibody panel of antibodies 7H11, 24C4 and 1A10.

9. The staphylokinase derivatives as claimed in claim 5 having the amino acid sequence as depicted in FIG. 1 (SEQ ID NO: 2) in which one or more amino acids in one or more clusters of amino acids selected from the group consisting of amino acids 5 and 6; 8 and 10; 11, 13 and 14; 22; 33 and 35; 35 and 38; 46 and 50; 57–59; 61 and 65; 65 and 69; 74, 75 and 77; 80 and 82; 86 and 88; 93 and 94; 96–98; 99 and 100; 99, 100 and 102; 108 and 109; 115, 118 and 119; 119 and 121; 130; and 134–136, have been replaced by alanine thus reducing the reactivity of the derivative with a monoclonal antibody panel of antibodies 17G11, 30A2, 3G10, 7H11, 24C4 and 1A10.

10. A method for producing the staphylokinase derivatives as claimed in claim 5, comprising the steps of:

a) preparing a DNA fragment comprising at least the part of the coding sequence of Staphylokinase that provides for its biological activity;

b) performing in vitro site-directed mutagenesis on the DNA fragment to replace one or more codons for wild-type amino acids by a codon for another amino acid;

c) cloning the mutated DNA fragment in a suitable vector;

d) transforming or transfecting a suitable host cell with the vector; and e) culturing the host cell under conditions suitable for expressing the DNA fragment.

11. A method as claimed in claim 10, wherein the DNA fragment is a 466 bp EcoRI-HindIII fragment of the plasmid pMEX602SAK, the in vitro site-directed mutagenesis is performed by an oligonucleotide-directed mutagenesis system using the plasmid pMa/c and the repair deficient *E. coli* strain WK6MutS, and the mutated DNA fragment is cloned in *E. coli* strain WK6.

12. A pharmaceutical composition comprising at least one of the staphylokinase derivatives as claimed in claim 5 together with a suitable excipient.

13. The pharmaceutical composition as claimed in claim 12 for treating arterial thrombosis.

* * * * *

UNITED STATES PATENT AND TRADEMARK OFFICE
CERTIFICATE OF CORRECTION

PATENT NO. : 5,695,754
DATED : December 9, 1997
INVENTOR(S) : Desire Collen

It is certified that error appears in the above-identified patent and that said Letters Patent is hereby corrected as shown below:

Column 1 Line 55 "sak0C" should read --sakØC--.

Column 2 Line 3 "sak0C" should read --sakØC--.

Column 2 Line 44 "with 40" should read --within 40--.

Column 2 Line 62 "12-42 1µg/ml" should read --12-42 µg/ml--.

Column 2 Line 65 "pilot trail" should read --pilot trial--.

Column 3 Line 34 "binding at" should read --binding of--.

Column 3 Line 63 "derivatives" should read --derivative--.

Column 4 Line 3 "82in" should read --82 in--.

Column 4 Line 7 "(SEQ. ID NO:  )" should read --(SEQ. ID NO: 2)--.

Column 5 Line 55 "0.15M" should read --0.15 M--.

Column 5 Line 59 "6 o 30" should read --6 to 30--.

Column 5 Line 60 "3 µl" should read --5 µl--.

Column 5 Line 63 "consists" should read --constants--.

Column 6 Line 2 after "17G11" insert comma.

Column 7 Line 2 "Lift Technologies" should read --Life Technologies--.

Column 7 Line 39, after "oligonucleotide" insert period and at beginning of Column 7 Line 40, delete period.

Column 7 Line 4T, "oligonuleotide" should read --oligonucleotide--.

UNITED STATES PATENT AND TRADEMARK OFFICE
CERTIFICATE OF CORRECTION

PATENT NO. : 5,695,754
DATED : December 9, 1997
INVENTOR(S) : Desire Collen

It is certified that error appears in the above-identified patent and that said Letters Patent is hereby corrected as shown below:

Column 8 Line 6 "ere" should read --were--.

Column 8 Line 57 after "SakSTAR" insert comma.

Column 9 Line 24 "31 percent" should read --51 percent--.

Column 10 Line 4 between "Newbury" and "Ohio" insert comma.

Column 10 Line 32 "land with" should read --and with--.

Column 11, Table 1, under heading "Epitope cluster I" second column heading "2GA2" should read --26A2--.

Columns 11-12, Table 1, under heading "Epitope cluster III" row "M8": Insert "110" in column labeled "Spec.Act. $(x\ 10^3/mg)$" and move remaining numbers over to the right.

Column 11, Table 2, in title, "staphyloidnase" should read --staphylokinase--.

Column 12, Table 2, in title, "staphyloidnase" should read --staphylokinase--.

Column 11, Table 2, Line 46, in title, "myocardinal" should read --myocardial--.

Column 12, Table 2, Line 46, in title, "myocardinal" should read --myocardial--.

Column 13 Line 19, Ref. No. 2, "Basis" should read --Basic--.

Column 13 Line 53, Ref. 13, "Geriach" should read --Gerlach--.

Column 13 Line 63, Ref. 16, "Gührs" should read --Gührs--.

UNITED STATES PATENT AND TRADEMARK OFFICE
CERTIFICATE OF CORRECTION

PATENT NO.  : 5,695,754
DATED       : December 9, 1997
INVENTOR(S) : Desire Collen It is certified that error appears in the above-identified patent and that said Letters Patent is hereby corrected as shown below:

Column 13 Line 63, Ref. 16, after "Birch-Hirschfeld" insert --E--.

Column 14 Line 63, Ref. 29, "Röcker" should read --Röcker--.

Column 15 Line 14, Ref. 35, "Jönsson" should read --Jönsson--.

Column 15 Line 19, Ref. 36, "Löfas" should read --Löfas--.

Column 15 Line 25, Ref. 38, "Karisson" should read --Karlsson--.

Seq. Listing, Column 15, "(2)" second occurrence (INFORMATION FOR SEQ ID NO: 2:) should read --(3)--.

Claim 5 Column 17 Line 43 "derivative" should read --derivatives--.

Claim 5 Column 17 Line 52 "115." should read --115,--.

Signed and Sealed this

Fourteenth Day of April, 1998

Attest:

Attesting Officer

BRUCE LEHMAN
Commissioner of Patents and Trademarks